United States Patent [19]

Gross

[11] Patent Number: 5,722,948
[45] Date of Patent: Mar. 3, 1998

[54] COVERING FOR AN OCULAR DEVICE

[76] Inventor: Fredric J. Gross, 7338 Millbrook Rd., Norfolk, Va. 23505

[21] Appl. No.: 549,506
[22] Filed: Feb. 14, 1996
[51] Int. Cl.[6] ........................................... A61M 5/00
[52] U.S. Cl. .................................................... 604/8
[58] Field of Search ........................ 604/8–10, 289, 604/294; 602/74; 606/107

[56] References Cited

U.S. PATENT DOCUMENTS

| | | | |
|---|---|---|---|
| 3,960,150 | 6/1976 | Hussain et al. | 604/294 X |
| 4,570,626 | 2/1986 | Norris et al. | 602/74 X |
| 4,863,457 | 9/1989 | Lee | 604/294 X |
| 5,178,604 | 1/1993 | Baerveldt et al. | 604/294 X |
| 5,346,464 | 9/1994 | Camras | 604/294 X |
| 5,411,473 | 5/1995 | Ahmed | 604/294 X |
| 5,520,631 | 5/1996 | Nordquist et al. | 604/8 |

FOREIGN PATENT DOCUMENTS

| | | | |
|---|---|---|---|
| 0138564 | 4/1985 | European Pat. Off. | 606/107 |
| 1529143 | 10/1978 | United Kingdom | 604/294 |

*Primary Examiner*—Mary Beth Jones
*Attorney, Agent, or Firm*—McAulay Fisher Nissen Goldberg & Kiel, LLP

[57] ABSTRACT

A man-made covering compatible with the sclera of an eye for use with an ocular aqueous shunting tissue-implantable, fluid-dissipating device, having a tubular member with an outside diameter of between 0.60 mm to 0.80 mm. The covering generally has a dimension of approximately 2 mm to 5 mm along one direction and approximately 4 mm to 9 mm along another dimension and a minimum thickness at one end and approximately between 0.80 mm to 1.20 mm at the other end.

20 Claims, 1 Drawing Sheet

COVERING FOR AN OCULAR DEVICE

BACKGROUND OFT HE INVENTION

1. Field of the Invention

This invention relates to glaucoma implant surgery. More particularly, this invention is concerned with glaucoma implant surgery in which a patch graft made from man-made material is used. More specifically, the invention is also concerned with the use of a material having an unlimited shelf-life such as a plastic or synthetic material to cover the extraocular tube portion of aqueous shunting devices after implantation thereof.

2. Description of the Prior Art

Aqueous shunting devices, also known as glaucoma implants, are being used to treat refractory glaucomas with increasing success and frequency. The implants typically consist of a flexible silastic tube attached to a plate which is secured to the sclera. The tube is inserted into the anterior segment of the eye and provides a channel for aqueous humor outflow to the scleral plate which forms a filtering bleb.

To date, donor sclera, donor dura fascia lata and pericardium patch grafts have been used to cover the extraocular tube portion of aqueous shunting devices after the implantation thereof. Ophthalmol Vis Sci 1994; 4:1424).

Silicone and silastic implants have been shown to be well tolerated when implanted around the eye (glaucoma implants, scleral buckles). Other synthetic materials such as Dacron® and GORTEX® have been shown to be well tolerated in humans as vascular implants, but not in connection with glaucoma implants.

Aqueous shunting procedures were introduced by Molteno in 1968 to treat refractory glaucomas. In the initial design, Molteno used an 8.5 mm acrylic plate attached to an acrylic tube which he expected would allow the formation of a bleb with free communication to the anterior chamber which would not shrink to an area less than that of the plate. Molteno found that this device was successful in controlling intraocular pressure in many patients who were otherwise poor surgical prospects. Still, problems related to early post-operative hypotony from overfiltration and intraocular pressure increases resulting from fibrous encapsulation of the filtering bleb limited the usefulness of this procedure. Over the past twenty-five years, design modifications and improvements in surgical technique have led to greater success and lower complication rates using the Molteno implant. In addition, other aqueous shunting devices have been introduced which offer unique features designed to facilitate implantation, improve pressure control, or reduce the acute post-operative hypotony associated with implant procedures.

Aqueous shunting procedures are typically reserved for patients with severe uncontrolled glaucoma who have failed previous glaucoma surgery. In addition, they appear to be advantageous as a primary procedure in patients with neovascular glaucoma. Recent studies suggest an increasing role for seton procedures in the management of advanced congenital and juvenile glaucoma, traumatic glaucoma, aphakic and pseudophakic glaucoma, post-keratoplasty glaucoma, and other secondary glaucomas. In eyes with useful remaining vision, setons may be preferable over cyclodestructive procedures which are associated with a high rate of visual loss and phthisis bulbi.

The Mokeno implant consists of a silicone tube with an external diameter of 0.63 mm connected to a rigid polypropylene plate which is 13 mm in diameter (surface area: 270 mm). Single or double plate implants are available. A dual-chamber single-plate implant which incorporates a pressure ridge on the upper surface of the episcleral plate has been introduced in an effort to reduce immediate post-operative hypotony and its related complications.

The Anterior Chamber Tube to Encircling Band, hereinafter "ACTEB", implant consists of a silastic tube with an external diameter of 0.64 mm connected to a #20 band 360 degrees in length (surface area; 350–450 mm). The band is placed under three or four rectus muscles creating a reservoir for aqueous drainage.

Krupin's Valve with Disc consists of a silastic tube with an internal diameter of 0.38 mm connected to an oval silicone plate measuring 13 mm×18 mm which is 1.75 mm thick. The tube incorporates a unidirectional and pressure sensitive slit valve (opening pressure 11 mmHg; closing pressure 9 mm Hg) which serves to maintain the anterior chamber depth and intraocular pressure in the immediate postoperative period.

Baerveldt's implant consists of a silicone tube with an internal diameter of 0.3 mm connected to a Barium-impregnated plate which is 1 mm thick. The implant plates are made with surface areas of 200 mm (20×13 mm), 350 mm (32×14 mm) and 500 mm (36×17.5 mm).

Ahmed's Glaucoma Valve consists of a silastic tube which is connected to an elliptical polypropylene body and plate with an anterior surface area of 184 mm (13 mm by 16 mm). The valve body contains a pressure sensitive membrane valve which consists of two opposed silastic sheets which separate to allow aqueous flow at an intraocular pressure of between 8–12 mm Hg.

Implantation of aqueous shunting devices requires careful attention to detail at every step of the procedure to improve results and minimize post-operative complications. Surgery can usually be performed under local anesthesia with a retrobulbar or peribulbar block. For a one-plate implant, a fornix-based or limbus-based conjunctival incision is created extending for 90 to 110 degrees centered between two rectus muscles. Implantation of the plate is slightly easier with a fornix-based flap; however, the conjunctival closure is more involved. If a fornix-based flap is created, one or two radial relaxing incisions are usually required to allow adequate exposure for insertion of the plate. With the conjunctiva and tenons retracted away from the globe to expose bare sclera, the implant is position between two rectus muscles so that the anterior edge is approximately 8 to 10 mm posterior to the limbus. With larger and oval shaped implants, the implant is inserted with its long axis directed toward the apex of the orbit and then rotated horizontally so that the tube points directly toward the anterior chamber. If a two-plate implant is used, one plate is positioned in each quadrant. The tube connecting the two plates may be passed under or over the intervening rectus muscle.

Once the implant has been appropriately positioned, each plate is secured to the globe with two non-absorbable sutures. Secure attachment to the underlying sclera is essential to prevent anterior to posterior or lateral migration of the implant during the post-operative period. Inadequate scleral fixation may also lead to retraction of the tube from the anterior chamber or expulsion of entire plate from the subconjunctival space.

After the plate is attached to the globe, the tube is laid across the cornea and cut with a sharp scissors to create a beveled edge. The tube should extend approximately 2.6 to 3 mm into the anterior chamber in order to minimize the risk of tube cornea touch or retraction out of the anterior chamber. A 23-gauge needle is used to create a track into the anterior chamber just anterior and parallel to the iris through which the tube is inserted. Occasionally insertion of the tube through the scleral track is difficult. A well-beveled tube end (30 to 45 degrees, bevel up) simplifies this procedure; however, a metallic insertion forceps which surrounds the distal end of the tube is available to facilitate this maneuver. It is also beneficial to fill the anterior chamber with viscoelastic to stabilize the anterior chamber depth and keep the eye firm during the insertion process. After the tube has been inserted into the anterior chamber, its position is checked carefully to insure that there is no tube cornea touch or iris incarceration. If the tube is malpositioned a new entry track should be created 2 mm to the side of the original track through which the tube should be reinserted. If the original entry site is leaking, the scleral opening should be sutured closed to avoid post-operative overfiltration and hypotony. If a two stage procedure is planned, the tube is sutured to the sclera and covered with tenons and conjunctiva. Five to six weeks later, the conjunctiva is opened to expose the tube which is then inserted into the anterior chamber as previously described.

A 6 mm by 6 mm scleral patch graft (although other size grafts may be used) is then prepared from banked sclera (human material). (Freedman J F, Opthalmalic Surgery 1987; 18:532–4). Surgeons would always opt for and choose the thinnest available piece of sclera, since it will be easier to handle and secure to the globe. Thick pieces of sclera are also more likely to cause dellen formation. The presently used patch size, which is made from man-made material, can vary and depends on the patient and the specific operation. The graft is positioned to overlie the tube insertion site into the anterior chamber and the limbal edge is thinned in order to avoid a surface irregularity of the limbus which can lead to dellen formation. The graft should completely cover the tube for 6–8 mm starting at the tube entry site extending posteriorly toward the plate(s) of the implant. Appropriate placement is necessary to avoid conjunctival melting over the tube which frequently requires removal of the implant and necessitates another glaucoma procedure. The scleral graft is usually secured to the globe with four interrupted nylon sutures which are placed at the corners of the graft. All suture ends should be buried beneath the scleral graft to prevent them from later eroding through the conjunctiva.

Recently, some surgeons have begun to use banked pericardium, or fascia lata (also human material) to cover the tube because of their greater availability, improved sterilization and easier handling in comparison to preserved donor sclera.

It has also been proposed to use dehydrated cadaveric dura mater and reference is made to an article by James D. Brandt, MD entitled "Patch Grafts of Dehydrated Cadaveric Dura Mater for Post-Shunt Glaucoma Surgery", published in Arch Ophthalmal Vol. III, October 1993, pages 1436–39, which clearly sets forth the problems with human material. While the cadaveric dura mater is set forth very favorably, it should be noted that the use of this material may be an anathema to some people.

After the graft has been placed, the conjunctiva and tenons are pulled over the plate, tube, and graft and secured into place. Prior to conjunctival closure, the limbal margin of the cornea may be cauterized in order to remove the epithelium and provide a bed to facilitate the attachment of the conjunctiva during the healing process. Wing sutures at both ends of the peritomy are recommended to approximate the conjunctiva at the limbus. A locked running VICRYL suture is useful in closing the radial relaxing incision.

Once the operation has been completed, the eye should be inspected to assure that the implant plate, scleral graft, and intraocular portion of the tube are in good position. If a valved implant is used, fluid or air should be injected through the paracentesis track in order to confirm that the implant is functioning. Fluorescein drops can be used to inspect the bleb for leaks. Any buttonholes which are found in the conjunctiva should be closed with sutures on a vascular needle in a watertight fashion. At the conclusion of the procedure, Atropine Sulfate 1% drops are instilled topically and the surgeon's preferred antibiotic and steroid regimen is administered.

SUMMARY OF THE INVENTION

An object of the invention is to provide for a material which is sterile, easy to use by a surgeon and is of low cost.

A further object of this invention to provide for a man-made material such as a synthetic material graft which can be used in place of human material, such as donor human tissue for the purpose of covering the external tube portion of aqueous shunting devices.

Another object of the invention is to provide a device formed from man-made material which is well tolerated by the human body and which will also prevent shunt migration, by fitting snugly around the shunt tube and allowing easy attachment to the underlying sclera.

A further object of the invention is to provide for a material which can be used in lieu of cadaveric material.

Yet another object of this invention is to create a synthetic graft which covers the tube portion of an implanted aqueous shunting device creating a smooth contoured surface, molded to the contour of the eye which will not induce conjunctival melting or dellen formation.

This invention proposes to use grafts made of non-human synthetic material. Several sizes will be available as determined by demand. Based on current methodology, 6 mm by 6 mm to 8 mm by 8 mm grafts are considered to be useful. The grafts will be individually packaged.

More specifically, the non-human synthetic material can have a dimension of approximately 2 mm to 5 mm along one direction, about 4 mm to 9 mm along another dimension and having a minimum thickness at one end depending on manufacture and between 0.8 mm to 1.2 mm at the other end.

It is preferred that the dimension along the one direction is between 3 mm and 5 mm, about 5 mm to 8 mm along the other direction orthogonal to the one direction and with a thickness of approximately 0.20 at the one end and between 0.8 mm to 1.0 mm at the other end. The material is sufficiently flexible to curve and assume the curvature of the eye or globe.

Since the material is man-made, no problems will arise due to bunching or possible improper fitting.

A feature of the invention is that with the use of synthetic patch grafts, neither human donor tissue nor cadaveric material would be necessary, and one would not have to be concerned with the availability of human donor tissue nor cadaveric, as well as the excess costs incurred in connection with therewith.

A synthetic patch graft for glaucoma implant surgery made from material such as silicone, silastic, Dacron®, GORTEX®, or other well-tolerated material would offer many advantages, because it would be possible to avoid the current use of human donor tissues or cadaveric material. Moreover, the use of man-made synthetic material in place of human or cadaveric material has the additional advantages in that it:

1. is easily available in a large supply;
2. can be manufactured to specification;
3. avoids the risk of transmission of infectious diseases (HIV, etc.);
4. is cost effective; and
5. does not require special storage.

With the use of a man-made donor material, uniformity in connection with the thickness of the material is obtainable and the problems associated with defects in human donor material would be avoided.

From an analysis of the history and procedures, it is evident that human material which is used at present presents problems.

With the use of non-human and non-cadaveric materials, there is substantially no risk of infection. Other advantages of non-human material is that it:

1. can be designed to specifications with uniform production (avoiding the inconsistency, variable thickness and rigidity of human tissue);
2. eliminates the need for contouring of the tissue by the surgeon;
3. allows for easier attachment to the globe;
4. has a thin anterior edge contour which will reduce dellen formation;
5. can be contoured to fit over the tube more smoothly, improving conjunctival contour;
6. yields a superior cosmetic result because human scleral grafts are white and stand out from the surrounding tissue;
7. can be contoured to allow easy placement over all commercial shunts (i.e., Krupin, Baerveldt, Ahmed, Molteno);
8. obviates problem of non-availability of human or cadaveric tissues;
9. avoids problems of melting human tissues; and
10. provides a contour fit around the shunt tube reducing the risk of shunt migration.

In the prior art procedures, human patch material is usually cut free-hand and can result in non-uniformity. With the man-made material, the patch can be manufactured to specific specifications.

To these ends, the invention consists in the provision of a covering for use with an ocular aqueous shunting tissue-implantable, fluid-dissipating device, having a tubular member with an outside diameter of between 0.60 to 0.80 mm, the covering comprising a man-made material compatible with the sclera of an eye and having a dimension of at least 3 mm along one direction and about 5 mm along another dimension and having a thickness of at least 0.20 mm at one end and between 0.8 mm to 1.0 mm at the other end.

The covering can also be formed as a wedge having two spaced sides of different heights, the wider of one said sides being 0.75 mm and the narrower of the other of said spaced sides being 0.25 mm, with the lower profile being placed near the cornea of the eye.

The covering includes a trough and an opening in the other end opening into the trough for receiving the tube. The trough extends substantially the full distance between the ends, but short of one end to provide for a complete closure over the tube along which the man-made material overlies the tube.

DETAILED DESCRIPTION OF THE INVENTION

Figure 1:
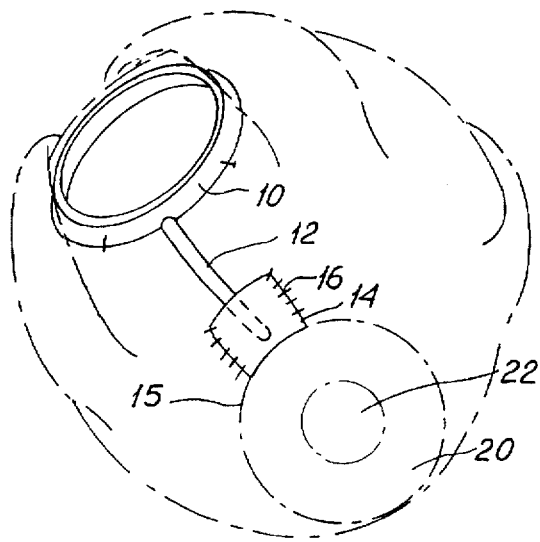
FIG. 1 illustrates a typical prior art aqueous shunt using conventional human donor sclera.

Referring now more particularly to the drawing on which like parts in the various figures are indicated with the same reference numeral and similar parts are referred to with different reference numerals, and reference is now made to FIG. 1, which illustrates a typical example of a prior art aqueous shunting device, plate 10, tube 12 and a scleral patch 14 of human material proximate to the limbus 15 of the eye 18. Patch 14 is stitched by means of sutures 16 to the eye 18 proximate to the iris 20 surrounding the pupil 22. As noted heretofore, the patch 14 can also be made from cadaveric dura, pericardium or fascia lata material.

Figure 2:
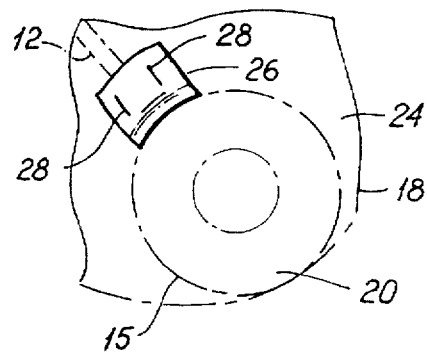
FIG. 2 is a schematic view of the invention somewhat similar to FIG. 1, but with portions omitted and an illustration of a man-made patch according to the invention used in connection with a conventional aqueous shunt device and illustrating the use of mattress stitching to secure the device to the sclera.

FIG. 2 shows a portion of an eye 18, tube 12 in dotted outline, the human sclera 24 and a man-made material 26, schematically shown, stitched by means of mattress stitching 28 on both sides to the human sclera 24 of a patient whose eye 18 is being treated. The shunt plate 10 (not shown in FIG. 2) is attached to the eye 18 in a conventional manner and forms no part of this invention.

Figure 3:
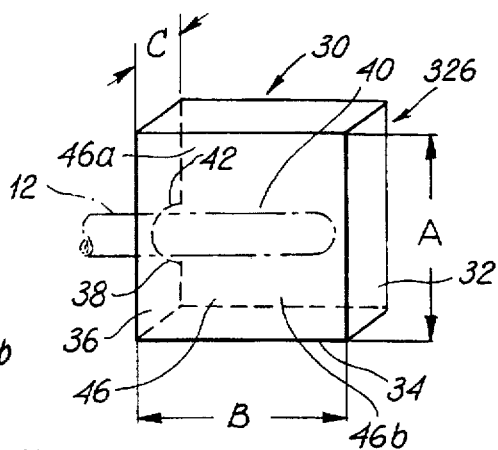
FIG. 3 is a perspective view of one embodiment of the man-made patch according to the invention shown as a square configuration and a uniform thickness, but which can have variable dimensions.

In FIG. 3, one embodiment of a plastic or man-made material 32*6* is shown as a square man-made material 30 overlying tube 12 prior to the stitching to the sclera 24. While FIG. 3 shows the man-made material having a square configuration, the material may also have a rectangular configuration. It is preferred that side 32 have a long dimension A with a length of between 4 mm and 6 mm and a short dimension C, and that side 34 have a long dimension B with a length of 6 mm to 10 mm, preferably between 8 mm and 10 mm and a short dimension C, and the short dimension noted with the letter C for providing for a thickness or height dimension of approximately 1.0 mm to provide for a cave or cavernous portion 40 to overlie and cover tube 12 on the sides as well as the top so as to conform as nearly as possible to the outer surface portion of tube 12. The term cave portion is used because while there is a tunnel-like opening 42 in side 38, providing an entrance for tube 12, there is no exit through side 32. Tube 12 does not extend the full length of side 34 or dimension B, and terminates 1.0 mm to 2 mm from side 32 because it enters into the eye and the cave terminates at 48.

Base portion 46 is defined by dimensions A and B and is provided with two side portions 46*a* and 46*b* on opposite sides of the cave 40.

Figure 5:
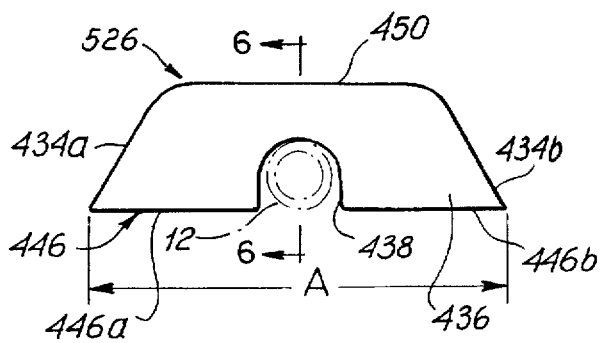
FIG. 5 is a front view of the man-made patch according to the invention illustrating a front partial trapezoidal configuration and showing a curved opening in the form of a cave to provide a cut-out portion for the tube of the aqueous shunting device.
Figure 6:
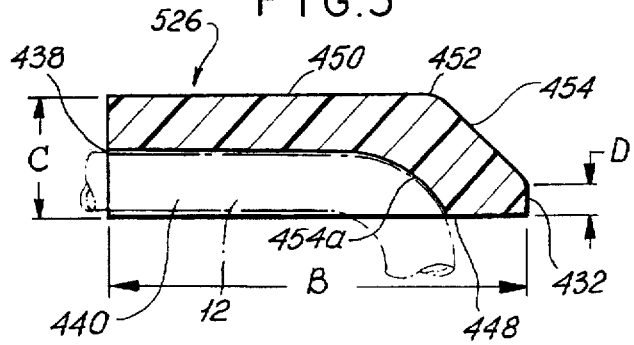
FIG. 6 is side view of showing a top portion or roof as having a straight portion and then a partially sloped configuration from rear to the front.
Figure 4:
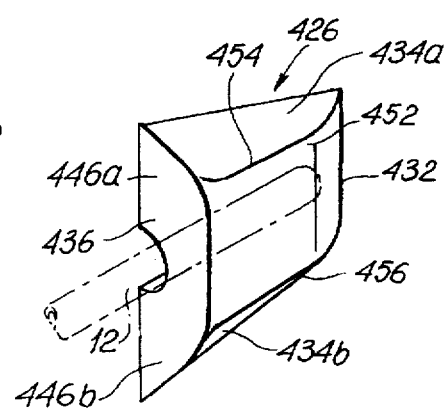
FIG. 4 is a perspective view of another embodiment of the man-made patch according to the invention shown as having a configuration which is partially trapezoidal in configuration and a non-uniform thickness.

Various different embodiments of the plastic or man-made material may be provided, and in FIGS. 4 to 6, another embodiment is shown with a different configuration. In this embodiment, man-made material 26 is designated 426 and is shown with a partial trapezoidal configuration having curved portions to provide for a better conformity with the outer portions of the eye.

In the FIGS. 4 to 6 embodiment, parts or portions similar to that in the FIG. 3 embodiment will be designated with similar reference numerals prefixed with the number 4 or raised by 400.

As best seen in FIG. 5, a rear side view of material 426 is shown with a curved opening portion 438 of the cave 440 to overlie tube 12 of the plate 10 of the conventional shunt.

As best seen in FIG. 6, tube 12 passes underneath from curved opening portion 438 at the rear end and then extends longitudinally thereof and curves under inner portion 454a of side 454. The material includes a base portion 446 which overlies the sclera of the eye and base side portions 446a and 446b, and two trapezoidally-shaped sides 434a and 434b, front portion 432 and rear portion 436. Rear side 438 may have a height or width dimension D of 0.50 mm to 1.00 mm, and preferably a height dimension of 0.75 mm to 1.00 mm to accommodate tube 12.

As seen in FIGS. 4 and 5, the front side 432 preferably has a preferred height dimension D of approximately 0.20 mm and can vary between a dimension as thin as possible depending upon the material, and desirably between 0.25 mm and 0.50 mm and preferably about 0.20 mm, because tube 12 does not extend through, but terminates at 448 and about 1 mm to 2 mm short of front side 432.

The man-made material can have a substantially trapezoidal cross-sectional shape in a plane substantially perpendicular to the longitudinal axis of tube 12, or along the dimension B, and also a partially trapezoidally-shaped cross-section in a plane parallel to the longitudinal axis of tube 12 and substantially parallel to the base 446. Base 446 can be considered to be the lower base of the trapezoidally-shaped configuration, and upper base 450 which in the FIGS. 4 to 6 embodiment is smaller than lower base 446. Upper base 450 extends substantially parallel to a lower base 446, then at point 452 slopes downwardly and forms side 454 which connects sides 432 and upper base 452. Upper base 452 and side 454 are connected with sides 434a and 434b. The distance C between bases 446 and 450 may vary between 0.50 to 1.00 mm, and at least 0.75 mm is preferred to accommodate tube 12, which has an outer diameter of about 0.60 mm to 0.65 mm.

FIG. 6, which shows a side view with height dimension C, tube 12 in cave 440 indicates a configuration of tube 12 as it enters the eye so that there is a complete covering of tube 12 except from the area of entry into the eye. The sides 434a and 434b can curve directly into top base 450 and the lines 454 and 456 are intended to show curved portions. Also rear side 446 may have a dimension A greater than the dimension A of front side 432 so that there is a narrowing as the man-made material approaches the limbus 15 with a sufficient amount of the man-made material overlaying the tube.

Glaucoma surgeons have generally been concerned with the "bleb", the subconjunctival drainage space created by the surgeon. A great deal of work has been done in connection with tissue-implantable fluid dissipating devices, but heretofore surgeons have used human material to cover the fluid-dissipating devices, with all of the disadvantages in connection therewith.

The use of man-made material completely eliminates the risk of infection associated with the use of human origin material in connection with the fluid-dissipating devices. Clearly, there are many advantages in the use of man-made material in connection with the tube that communicates with the cavity and the anterior chamber. Specifically, the cave, cavity or trench in the man-made material which overlies tube 12 provides for a neat covering so that heaping or bunching associated with the use of human material is avoided, reducing the risk of corneal dellen formation. With human or cadaveric material, the material just lies on top of tube 12 and does not provide the close conformity and uniformity which can be provided with the man-made material according to the invention. The use of a plastic material also facilitates attachment of the graft to the sclera. Because a plastic graft has greater rigidity and shape maintaining properties than human material, two mattress sutures are adequate to secure it to the sclera. The knots may be rotated into the plastic material, eliminating the problems associated with erosion of suture knots through the conjunctiva.

The tube extends from the plate to the limbus about 8 mm to 10 mm. The plate portion is about 8 mm to 12 mm. The term cave has been used to define the volume through which the tube is placed. It is in effect also an upside-down trough.

While various different suggested sizes have been shown, it should be noted that with the use of man-made material, the surgeon can modify the device by cutting the material to the desired dimensions. As is clearly evident, a sheet of plastic material can be made which is supplied in rolls having one thickness at one side and a different thickness at the other side to provide for a trapezoidal-like shape along at least one and possibly two different dimensions or sides so as to provide two bases of different configuration. The surgeon, when cutting the plastic or man-made material, can cut any shape desired, and, if necessary, cut a patch material in another trapezoidal configuration as well as a square or rectangular or any other desired configuration. It is also possible to smooth the edges into a curve as part of the manufacturing process.

It will be obvious to those skilled in the art that various changes and modifications may be made thereon without departing from the scope of the invention.

I claim:

1. A covering for use with an ocular aqueous shunting tissue-implantable, fluid-dissipating device, having a tube component with an outside diameter of between 0.60 to 0.80 mm, the covering comprising a material compatible with the sclera of an eye and having a dimension of approximately 2 mm to 5 mm along one direction and about 4 mm to 9 mm along another dimension and having a tapered configuration with a minimum thickness at one end and between 0.8 mm to 1.2 mm at the other end and a cave overlying said tube component.

2. The covering as claimed in claim 1 wherein the dimension along said one direction is between 3 mm to 5 mm and about 5 mm to 8 mm along the other direction orthogonal to said one direction and the thickness is approximately 0.20 at the one end and between 0.80 mm to 1.0 mm at the other end, and the material is curved to cover the surface of the eye.

3. The covering of claim 1, wherein the covering has a substantially trapezoidal configuration having a lower base approximately 8 mm in length.

4. The covering as claimed in claim 1, wherein the covering is a man made material and is substantially trapezoidally shaped in two directions, along the longitudinal axis of the tube component and transversely to the longitudinal axis of the tube component.

5. The covering as claimed in claim 1, wherein the covering has a substantially trapezoidally shaped configuration in two directions with the sides merging into the smaller of the two parallel bases being smoothly curved in both directions, along the longitudinal axis of the tube component and transversely to the longitudinal axis of the tube component.

6. The covering as claimed in claim 1, wherein said covering is formed as a wedge having two spaced sides of different heights, the wider of said two spaced sides being 0.75 mm in width and the narrower of said two spaced sides being 0.25 mm in width with the lower profile being placed near the cornea of the eye.

7. The covering as claimed in claim 1, wherein the covering has a length and width dimension which is between 6 mm and 8 mm and a thickness dimension which is between 0.20 mm and 1.00 mm.

8. The covering as claimed in claim 1, wherein said material is made to conform to the shunting device used.

9. The covering as claimed in claim 1, wherein said material is attached to the sclera allowing simplified mattress stitching.

10. In a method for forming a covering for an ocular aqueous-shunting, tissue-implantable, fluid dissipating device, comprising:

forming a covering for the shunting device, covering the shunting device with said covering; and providing the covering with a cave to overlie the aqueous-shunting, tissue implantable fluid dissipating device.

11. In the method as claimed in claim 10, wherein the covering is provided with a width dimension which is between 3 mm and 8 mm and a length dimension of 7 mm to 10 mm and a thickness dimension which varies between a minimum thickness dimension at one end and 1.20 mm between an end opposite to said one end and said cave has a height of at least 0.60 mm to overlie the aqueous shunting tissue, implantable, fluid dissipating device.

12. In the method of claim 10, wherein the material is a man-made plastic material.

13. In the method of claim 11, wherein the cave has a longitudinal axis coaxial with the axis of a tube forming part of the fluid dissipating device.

14. In the method of claim 10, wherein the material is a plastic material or a synthetic material.

15. A covering for use with an ocular aqueous shunting tissue-implantable, fluid-dissipating device, having a tubular component with an outside diameter between 0.60 to 0.80 mm, the covering comprising a material compatible with a sclera of an eye and having a dimension of approximately 2 mm to 5 mm along one direction and a dimension of approximately 4 mm to 9 mm along another dimension and having a tapered configuration with a minimum thickness at one end and a thickness between 0.8 mm to 1.2 mm at the other end, said other end being provided with a cavernous opening for receiving said tubular component.

16. The covering as claimed in claim 15, including a cave overlying the tube component.

17. The covering as claimed in claim 15, including a trough, and said cavernous opening in said other end opening into said trough for receiving the tubular component.

18. The covering as claimed in claim 15, including a trough extending substantially the full distance between said ends, said cavernous opening, opening into said trough for the tubular component, but short of said one end to provide for a complete closure over the tubular component at the limbus.

19. A covering for use with an ocular aqueous shunting tissue-implantable, fluid-dissipating device, having a tube component with an outside diameter of between 0.60 to 0.80 mm, the covering comprising a material compatible with the sclera of an eye including a trough for said tube component, said material having a tapered configuration with a minimum thickness at one end and a thickness at the other end greater than the minimum thickness, and an opening in said other end opening into said trough for the tube component.

20. The covering as claimed in claim 19, wherein said trough extends substantially the full distance between said ends, but short of said one end to provide for a complete closure over the tube at the limbus.

* * * * *